(12) United States Patent
Nur et al.

(10) Patent No.: US 9,329,183 B2
(45) Date of Patent: May 3, 2016

(54) IMMUNOASSAY FOR THROMBIN DETECTION

(71) Applicant: Omrix Biopharmaceuticals Ltd., Rehovot (IL)

(72) Inventors: Israel Nur, Moshav Timmorim (IL); Nadav Orr, Mazkeret Batia (IL); Roni Mintz, Moshav Shafir (IL)

(73) Assignee: Omrix Biopharmaceuticals Ltd., Rehovot (IL)

(*) Notice: Subject to any disclaimer, the term of this patent is extended or adjusted under 35 U.S.C. 154(b) by 0 days.

(21) Appl. No.: 14/710,097

(22) Filed: May 12, 2015

(65) Prior Publication Data

US 2015/0241430 A1    Aug. 27, 2015

Related U.S. Application Data

(62) Division of application No. 13/307,252, filed on Nov. 30, 2011, now Pat. No. 9,057,737.

(60) Provisional application No. 61/421,339, filed on Dec. 9, 2010.

(30) Foreign Application Priority Data

Dec. 9, 2010   (IL) ......................................... 209921

(51) Int. Cl.
*G01N 33/573* (2006.01)
*G01N 33/86* (2006.01)
*C07K 16/36* (2006.01)

(52) U.S. Cl.
CPC .............. *G01N 33/573* (2013.01); *C07K 16/36* (2013.01); *G01N 33/86* (2013.01); *G01N 2333/815* (2013.01); *G01N 2333/8128* (2013.01); *G01N 2333/974* (2013.01)

(58) Field of Classification Search
CPC ........ G01N 33/573; G01N 33/86; C07K 16/36
See application file for complete search history.

(56) References Cited

U.S. PATENT DOCUMENTS

| 4,753,875 A | 6/1988 | Ryan |
| 5,296,532 A | 3/1994 | Haerzschel et al. |
| 5,688,507 A * | 11/1997 | Weitz et al. ............... 424/184.1 |

FOREIGN PATENT DOCUMENTS

| EP | 0 479 721 | * 9/1991 | ............ C07K 15/28 |
| EP | 0479721 | 4/1992 | |
| JP | 58-129998 | 8/1983 | |
| JP | 2001-103966 | 4/2011 | |

OTHER PUBLICATIONS

Bayer, E.A. et al 'Chapter 11—The Avidin-Biotin System' *Immunoassay* Academic Press (1996) pp. 237-267.

(Continued)

*Primary Examiner* — Gail R Gabel
(74) *Attorney, Agent, or Firm* — David R. Crichton (57) ABSTRACT

The invention relates to an in vitro immunoassay for quantifying thrombin in a sample comprising anti-thrombin III (AT-III) and thrombin. The method comprises the following steps: contacting the sample with a small molecule that recognizes the substrate binding site of thrombin; contacting the thrombin with a thrombin specific antibody raised against a thrombin blocked in the active site; and measuring the level of bound antibody.

8 Claims, 4 Drawing Sheets

(56) References Cited

OTHER PUBLICATIONS

Bichler J. et al 'Determination of thrombin-hirudin complex in plasma with an enzyme-linked immunosorbent assay' Blood Coagulation & Fibrinolysis (1991) vol. 2, No. 1 pp. 129-133.
Butler, J.E. 'Chapter 9—Solid Phases in Immunoassay' *Immunoassay* Academic Press (1996) pp. 205-225.
Campbell, A.M. 'Chapter 5—Production and Purification of Antibodies' *Immunoassay* Academic Press (1996) pp. 95-115.
Chan, D.W. 'Chapter 21—Automation of Immunoassays' *Immunoassay* Academic Press (1996) pp. 483-504.
Chang, J-Y. 'The Hirudin-binding Site of Human α-Thrombin. Identification of lysyl residues which participate in the combining site of hirudin-thrombin complex.' J. Biol. Chem. (1989) vol. 264, No. 13 pp. 7141-7146.
Chard, T. 'Chapter 12—Radioummunoassay' *Immunoassay* Academic Press (1996) pp. 269-285.
Chen, H-Y et al 'Thrombin titration for determination of improved activity of hurdin' Biotechnology (2002) vol. 12, No. 6 pp. 24-25.
Christopoulos, T.K. et al 'Chapter 10—Immunoassay Configurations' *Immunoassay* Academic Press (1996) pp. 227-236.
Christopoulos, T.K. et al 'Chapter 14—Fluroescence Immunoassays' Immunoassay Academic Press (1996) pp. 309-335.
Diamandis, E.P. et al 'Chapter 24—Development of In-House Immunoassays' Immunoassay Academic Press (1996) pp. 555-568.
Elgue, G. et al 'The Use of a Commerical ELISA for assay of thrombin-antithrombin complexes in purified systems' Thrombosis and Haemostasis, Schattauer GmbH (1990) vol. 63, No. 3 pp. 435-438.
Geiger, R.E. et al 'Chapter 16—Bioluminescence Immunoassays' Immunoassay Academic Press (1996) pp. 355-362.
Gosling, J.P. 'Chapter 13—Enzyme Immunoassay' Immunoassay Academic Press (1996) pp. 287-308.
Griffith, M.J. 'Kinetics of the Heparin-enhanced Antithrombin III/ Thrombin Reaction. Evidence for a template model for the mechanism of action of heparin.' J. Biol. Chem. (1982) vol. 257, No. 13 pp. 7360-7365.
Hinton, P.R. et al 'Chapter 6—Antibody Engineering' Immunoassay Academic Press (1996) pp. 117-164.
Huntington, J.A. 'Molecular recognition mechanisms of thrombin.' J. Thromb. Haemost. (2005) vol. 3 pp. 1861-1872.
Ishikawa, E. 'Chapter 8—Labeling of Antibodies and Antigens' Immunoassay Academic Press (1996) pp. 191-204.
Kohen, F. et al 'Chapter 19—Noncompetitive Immunoassay for Small Molecules' Immunoassay Academic Press (1996) pp. 405-421.
Kricka, L.J. 'Chapter 15—Chemiluminescence Immunoassay' Immunoassay Academic Press (1996) pp. 337-353.
Kricka, L.J. 'Chapter 18—Simultaneous Multianalyte Immunoassays' Immunoassay Academic Press (1996) pp. 389-404.
Markwardt, F. et al. The Influence of Synthetic Thrombin Inhibitors on the Thrombin-Antithrombin Reaction. Thrombosis Research (1973) vol. 2, No. 4 pp. 343-348.
Marmer, D.J. et al 'Chapter 17—Nephelometric and Turbidimetric Immunoassay' Immunassay Academic Press (1996) pp. 363-387.
Pandey, S. 'Hybridoma Technology for Production of Monoclonal Antibodies' International Journal of Pharmaceutical Sciences Review and Research (2010) vol. 1, Issue 2. pp. 88-94.
Rose, T. et al 'Three-dimensional Modeling of Thrombin-Fibrinogen Interaction' Journal of Biological Chemistry (2002) vol. 277 No. 21 pp. 18875-18880.
Zoldhelyi, P. MD, et al 'Persistent Thrombin Generation in Humans During Specific Thrombin Inhibition with Hirudin' Circulation (1994) vol. 90, No. 6 pp. 2671-2678.
International Search Report re: PCT/IL2011/000911 dated Mar. 6, 2012.
Written Opinion re: PCT/IL2011/000911 dated Jun. 12, 2013.
Steinmetzer, T. et al 'Rationales Design von Thrombinhemmstoffen: Von Fibrinogen and Hirudin zu synthetischen Antikoagulanzien' Pharmazie in Unserer Zeit (2004) vol. 33, No. 3 pp. 196-205.
Communication from European Patent Office dated Apr. 10, 2015 re: 11804825.5.
International Preliminary Report on Patentability re: PCT/IL2011/ 000911 dated Jun. 12, 2013.
Malovichko, M.V. et al 'Ligand Binding to Anion-binding Exosites Regulates Conformational Properties of Thrombin' J. Biol. Chem. (2013) 288(12) pp. 8667-8678.
Product Cat3: SAHT-AP, 'Sheep Anti-Human Thrombin' Affinity Biologicals Inc., Canada, Jul. 1, 2015, 1 page.

\* cited by examiner

IMMUNOASSAY FOR THROMBIN DETECTION

This application is a divisional of U.S. application Ser. No. 13/307,252, filed on Nov. 30, 2011, now U.S. Pat. No. 9,057,737, which claims priority of U.S. Provisional Application No. 61/421,339, filed Dec. 9, 2010, the disclosure of which is hereby incorporated by reference herein. The present application also claims benefit of Israeli Patent Application Number IL209921, filed Dec. 9, 2010.

FIELD OF THE INVENTION

The invention relates to an immunoassay for quantifying thrombin in a sample comprising anti-thrombin III (AT-III).

BACKGROUND OF THE INVENTION

Thrombin (α-thrombin) is an endolytic serine protease that plays a major role in the coagulation cascade or thrombus formation. Thrombin is produced by the enzymatic cleavage of the zymogen prothrombin. The cleavage is carried out by activated factor X (factor Xa). Human thrombin is composed of a light chain (having a molecular weight of ~6 kDa) and a heavy chain (having a molecular weight of ~31 kDa). Thrombin comprises an active site which is located within the heavy chain. Thrombin has a high specificity for protein substrates having arginine bonds and its main substrate is fibrinogen. Thrombin binds fibrinogen and converts it into fibrin. Thrombin also activates protein C, platelets, factor XIII and plasma procarboxypeptidase B (TAFT).

Normally, thrombin activity is inhibited in plasma. The main inhibitor of thrombin present in plasma is anti-thrombin III (AT-III) and to a lesser extent heparin cofactor II. The rate of inhibition by both of these inhibitors is profoundly increased in the presence of optimal concentrations of heparin. Other physiological inhibitors of thrombin are α2-macroglobulin, and α1-antitrypsin1-4.

AT-III inhibits the coagulation cascade by binding thrombin and factor Xa. The inhibitory activity of AT-III is markedly increased by the presence of heparin. The normal antithrombin III concentration in human blood plasma is high and is of approximately 0.12 mg/ml. Thrombin inactivation occurs as a result of trapping of thrombin in an equimolar complex with AT-III. Formation of the complex prevents accessibility of the active site of the thrombin to its substrate. Formation of an anti-thrombin III-thrombin complex involves an interaction between the thrombin and a specific reactive peptide bond within AT-III. In human AT-III this bond is between arginine (arg) 393 and serine (ser) 394.

Abnormal high levels of thrombin in the circulation may trigger the coagulation cascade, consequently resulting in generalized coagulopathy. A method which enables fast and quantitative determination of the levels of thrombin in a tested biological sample, e.g. a blood sample, is of considerable biomedical interest. Fast and quantitative analysis of thrombin in plasma of humans and animal models may also be of high importance for safety assessments of experimental and routine usage of hemostats which include thrombin.

Detection of thrombin by immunoassay using thrombin specific antibodies, in a background of relatively large quantities of the pro-enzyme prothrombin, such as in a plasma sample, may be challenging.

U.S. Pat. No. 4,753,875 discloses a method for assaying thrombin, in which an excess of tagged thrombin inhibitor (e.g. tagged hirudin or tagged AT-III) is mixed in solution with a tested sample containing the thrombin to form a mixture of a tagged inhibitor-thrombin complex and free tagged inhibitor. Next, an anti-thrombin antibody is added to form complexes of tagged inhibitor-thrombin and thrombin specific antibody. The complexes are then separated from the free tagged inhibitor and the tag is measured. Exemplified is an assay for testing thrombin in a sample of plasma by adding 3H-hirudin and separating the complex thrombin-hirudin with thrombin specific antibodies coupled to cellulose. Thus, this test requires a step of complex separation e.g. using an additional step of affinity chromatography column separation.

U.S. Pat. No. 5,296,352 discloses monoclonal antibodies which are directed against and recognize the thrombin/hirudin-complex and derivatives thereof. U.S. Pat. No. 5,296,352 discloses the use of the monoclonal antibodies for detection of thrombin/hirudin complex. It is also disclosed that the monoclonal antibodies can be employed for detecting small amounts of spontaneously generated thrombin in a subject. The method includes injecting to the subject hirudin as a tracer followed by the measurement of the complex thrombin/hirudin formed with the aid of the monoclonal antibodies that recognize the complex. Exemplified is an ELISA assay for determination of the thrombin-hirudin complex present in plasma. This test requires injection of hirudin to the subject for testing thrombin.

There is a need for an in-vitro, easy, fast, and effective test for determining thrombin levels in a blood sample.

SUMMARY OF THE INVENTION

The invention relates to an in-vitro immunoassay for quantifying thrombin in a sample in the presence of anti-thrombin III (AT-III).

In one aspect, the immunoassay comprises the steps of: contacting the sample with a small molecule that recognizes the substrate binding site of thrombin; contacting the thrombin with a thrombin specific antibody raised against a thrombin blocked in the active site; and measuring the level of bound antibody.

In another aspect, the immunoassay comprises the steps of: contacting the sample with a small molecule that recognizes the substrate binding site of thrombin; adding to the sample a thrombin specific antibody, wherein the thrombin specific antibody is raised against a thrombin having a blocked active site; measuring the binding of the antibody to the thrombin; and determining the amount of thrombin present.

In one embodiment of the invention, the sample is a biological specimen selected from the group consisting of blood or blood components.

In another embodiment of the invention, the small molecule is selected from the group consisting of naturally occurring hirudin, synthetic hirudin variants, hirudin derivatives, recombinant hirudin variants, mimics and a combination thereof.

In a further embodiment, the thrombin specific antibody is a polyclonal antibody or a fragment thereof.

Yet in another embodiment of the invention, the antibody is raised against a thrombin having a blocked active site with a peptide selected from the group consisting of Phe-Pro-Arg-chloromethylketone (PPACK), 4-aminophenylpyruvic acid (APPA), 4-(2-aminoethyl)benzenesulfonyl fluoride (AEBSF) and a combination thereof.

Yet in another further embodiment of the invention, the immunoassay is a solid-phase immunoassay such as a sandwich immunoassay.

Yet in another further embodiment of the invention, determining the thrombin amount is carried out with a thrombin standard curve.

The invention also provides a kit for quantifying thrombin in a sample comprising anti-thrombin III (AT-III), the kit comprises a thrombin specific polyclonal antibody or a fragment thereof and a small molecule that recognizes the substrate binding site of thrombin, wherein the thrombin specific antibody is raised against a thrombin having a blocked active site.

DESCRIPTION OF EMBODIMENTS OF THE INVENTION

It was found according to the present invention that detection of thrombin by a thrombin specific immunoassay is compromised by interfering substances present in the plasma. It was also found that the interference detected in the plasma may, at least in part, be accounted to AT-III presence.

Also, it was surprisingly found according to the present invention that addition of thrombin to a sample containing hirudin together with AT-III resulted in an increase in the ability of the thrombin specific immunoassay to detect thrombin in the sample compared to the control sample lacking hirudin. These results indicated that hirudin enhances thrombin detection in the presence of anti-thrombin III.

These findings are surprising, in view that the binding site of hirudin and AT-III in the thrombin molecule are different and that hirudin, in contrast to AT-III, is a small molecule. The binding site of hirudin in thrombin overlaps with the fibrinogen binding site of thrombin (Chang J Y. The hirudin-binding site of human alpha-thrombin. Identification of lysyl residues which participate in the combining site of hirudin-thrombin complex. J Biol Chem. 1989 May 5; 264(13):7141-6; Huntington J A. Molecular recognition mechanisms of thrombin. J Thromb Haemost. 2005 August; 3(8):1861-72) whereas the binding site of AT-III overlaps with the catalytic site of thrombin (Griffith M J. Kinetics of the heparin-enhanced antithrombin III/thrombin reaction. Evidence for a template model for the mechanism of action of heparin. J Biol Chem. 1982 Jul. 10; 257(13):7360-5; and Markwardt et al. The influence of synthetic thrombin inhibitors on the thrombin-antithrombin reaction. Thrombosis research. 1973 Vol. 2, 343-348).

It was also found that addition of hirudin after mixing thrombin with AT-III resulted in an increase in thrombin detection compared to the control in the absence of hirudin. Hirudin reduces the interference encountered in a thrombin specific immunoassay when testing plasma samples or other samples comprising AT-III.

Without being bound to the mechanism, it seems that antigenic groups in thrombin are hidden and/or altered by the association of thrombin with AT-III, and that the addition of hirudin reduces the interference that AT-III exerts to the immunoassay, and thereby increases thrombin detection by the immunoassay.

These findings pave the way to the development of an immunoassay method that enables to determine the levels of thrombin under conditions of high AT-III levels, i.e. the prevailing condition found in plasma samples.

The invention provides an in vitro immunoassay for quantifying thrombin in a sample in the presence of AT-III, the method comprising the steps of: contacting the sample with a small molecule that recognizes the substrate binding site of thrombin such as the fibrinogen binding site; adding to the sample a thrombin specific antibody; measuring the binding of the antibody to the thrombin; and determining the amount of thrombin present.

The term "contacting" refers to a combining action that brings the small molecule into contact with the sample and more particularly to a combining action which brings the small molecule into contact with the thrombin in a manner that a binding interaction will occur between the small molecule and the thrombin present in the sample.

The term "small molecule" refers, for example, to a molecule with a molecular weight in the range of 400 to 100,000 Dalton, such as in the range of 400 to 50,000 Dalton or 400 to 40,000 Dalton or 400 to 8,000 Dalton or 400 to 1000 Dalton or 5,000 to 40,000 Dalton or 1,000 to 8,000 Dalton. The small molecule can be a synthetic mimic of hirudin having a similar tri-dimensional structure but exhibiting non duplicative sequence. A mimic of hirudin can be identified by screening e.g. a phage display library e.g. of random peptides. The screening can rely on competition of the peptides for the binding of hirudin to the substrate binding site in the thrombin. In one embodiment of the invention, an ELISA sandwich assay is used. A monoclonal antibody specific to the catalytic site of thrombin can be used to coat the ELISA microtiter plate. The plate is loaded with thrombin in blocking solution and the excess of thrombin is removed by several washes. Next, hirudin in blocking solution is loaded, and the excess of hirudin is washed away. Then, the hirudin bound to the plate (100% binding of hirudin) is detected using labeled polyclonal anti-hirudin antibodies. The bounding of hirudin can also be detected by using a labeled-hirudin e.g. 3H-hirudin. In test wells individual peptides are included in the ELISA, and the reduction of hirudin binding to the plates by the presence of a given peptide is indicative that the peptide is a possible mimicking peptide.

In one embodiment, the small molecule that recognizes the substrate binding site of thrombin inhibits at least 50% of the binding of thrombin to fibrinogen. The small molecules used in the method of the invention can be a peptide, a synthetic chemical compound, naturally occurring hirudin, synthetic hirudin variants, hirudin derivatives and/or recombinant hirudin variants which maintain the capability of binding to the substrate binding site of thrombin.

Variants comprise those hirudin polypeptides which contain amino acid substitutions, deletions and/or additions relative to the naturally occurring hirudin. Typically, the amino acid substitutions, deletions and/or additions do not alter the capability of the variant to bind to the substrate binding site of thrombin. The variant can also comprise non-naturally occurring amino acid residues.

Derivatives comprise glycosylated alteration, acylated alteration and/or other chemical alterations; non-amino acid substituents such as, for example, a reporter molecule and/or other ligand that are covalently or non-covalently bound to the amino acid sequence of the polypeptide.

A mimic comprises a very large number of small molecules that have the capability of reproducing the three dimensional conformation of hirudin without necessarily duplicating its structure. This mimicry need not be a complete duplication, and may be also an approximation thereof which is sufficiently similar to that of hirudin so that the mimic would be capable of binding thrombin.

In one embodiment of the invention, the small molecule is added into the tested sample in an amount that neutralizes the thrombin present in the sample. In another embodiment of the invention, the mole ratio between hirudin and thrombin in the sample is higher than or equal to 0.64 e.g. a mole ratio of 0.67, 1.27, 2.55, 5.10, 10.20, 12.76, 20.41, 25.52, 40.82, 51.05, 81.63, 102.56, 205.13, 410.26, 816.36, and 1632.65 or higher.

In one embodiment the thrombin is suspected to be present in the sample at about 1 unit and the hirudin is added at about 0.64 antithrombin units or higher.

Oftentimes, the terms "neutralizes" and "inhibits" are interchangeable.

The term "molecule that recognizes the substrate binding site of thrombin" refers to a molecule having an affinity to the substrate binding site of thrombin. In one embodiment of the invention, the substrate binding site of thrombin resides in exosite I. In another embodiment of the invention, one key element for binding is Tyr76, located about 20 Å away from the active site of thrombin as in the case of fibrinogen (Thierry Rose and Enrico Di Cera. Three-dimensional Modeling of Thrombin-Fibrinogen Interaction. JBC 2001 Vol 277 N21, 18875-1880).

The immunoassay of the invention can be carried out in any sample e.g. a biological specimen such as blood; blood components such as plasma and other blood derived fractions; other body fluids that comprise thrombin and anti-thrombin III; and the like.

The thrombin specific antibody used according to the invention is raised against a thrombin having the active site blocked. The term "a thrombin having a blocked active site" refers to a thrombin having a peptide bound to its active site. In one embodiment of the invention, the active site of thrombin resides in a cleft from P4 to P2' (Shown in FIG. 2 of Huntington J A. Molecular recognition mechanisms of thrombin. J Thromb Haemost. 2005 August; 3(8):1861-72). The peptide (called herein "blocking peptide") can be, for example, a tri-amino acid peptide derivative in the range of about 400 to 1000 Dalton, Phe-Pro-Arg-chloromethylketone (PPACK), 4-aminophenylpyruvic acid (APPA) or 4-(2-aminoethyl)benzenesulfonyl fluoride (AEBSF). The term "active site" is interchangeable with the term "catalytic site".

The thrombin specific antibody can be a monoclonal antibody, single chain, Fab fragments, including the products of a Fab immunoglobulin expression library, a polyclonal antibody or fragments thereof as long as they exhibit the binding specificity to thrombin and/or are capable of binding thrombin.

The term "polyclonal antibody" refers to a heterogeneous antibody population. This may comprise antibodies having antigen-binding functions specific for different epitopes within the thrombin. Polyclonal antibodies may be generated by immunizing an animal e.g. of mammalian species, such as rabbit, goat, donkey and sheep, with human thrombin. The thrombin used for the immunization can be prepared from purified human prothrombin. The routes of immunization include, but are not limited to, intradermal, intraperitoneal, subcutaneous, intramuscular, intracranial, and/or intravenous.

The term "monoclonal antibody" refers to an antibody preparation produced from a single clone of antibody-producing cells e.g. a single clone of hybridoma cells. Typically, monoclonal antibodies are produced by hybridoma technology. The term "hybridoma" refer to cells that have been engineered to produce a desired antibody in large amounts e.g. to produce monoclonal antibodies. To produce monoclonal antibodies, B-cells can be removed from the spleen of an animal (e.g. any mammalian specie) that has been immunized with thrombin. The thrombin used for the immunization can be prepared from purified human prothrombin. The routes of immunization include, but are not limited to, intradermal, intraperitoneal, subcutaneous, intramuscular, intracranial, and/or intravenous. The B-cells can then be fused with myeloma tumor cells that can grow indefinitely in culture. This fusion can be performed by making the cell membranes more permeable. The fused cells, being cancer cells, can multiply quickly and indefinitely and can produce large amounts of the desired antibodies. The antibodies produced can be tested for their specificity and affinity for thrombin. Methods of preparing monoclonal antibodies are known in the art, as are methods of determining their specificity (see for example Shivanand Pandey. "HYBRIDOMA TECHNOLOGY FOR PRODUCTION OF MONOCLONAL ANTIBODIES" International Journal of Pharmaceutical Sciences Review and Research. 2010; Volume 1, Issue 2:88-94).

Production and purification of polyclonal and monoclonal antibodies are well known in the art (Immunoassay, Eds. Eleftherios P Diamandis and Theodore K. Christopoulos, Academic Press 1996, Chapter 5). The thrombin specific antibody can be recombinant (Immunoassay, Eds. Eleftherios P Diamandis and Theodore K. Christopoulos, Academic Press 1996, Chapter 6).

Labeling antibodies for detection are well known in the art (Immunoassay, Eds. Eleftherios P Diamandis and Theodore K. Christopoulos, Academic Press 1996, Chapter 8).

"Detecting antibodies" and "labeled antibodies/labeling antibody" refer to antibodies that are capable of being discovered. The detecting antibody may be directly or indirectly (e.g. through another antibody) conjugated to a detectable signal or to a signal-generating moiety. The signal can be radioactive (e.g. radioactive iodine, tritium, carbon, sulfur or the like), colorimetric, fluorescent signal and the like. Signal-generating moieties that act on signal-generating substrates include, but are not limited to, horseradish peroxidase (HRP) [suitable substrates include 3,3',5,5'-tetramethylbenzidine (TMB); OPD; 2,2'-azinobis(3-ethylbenzothiazoline)-6-sulfonic acid diammonium salt]; alkaline phosphatase [suitable substrates include p-nitrophenyl phosphate disodium salt]; and β-galactosidase [suitable substrates include O-nitrophenyl-beta-D-galactopyranoside]. The signal may be amplified by using an Avidin-Biotin conjugation system.

Different types of immunoassays which rely on the binding interaction between the antigenic determinants of an antigen and the antigen-binding portion of the specific antibody are well known in the art (Immunoassay, Eds. Eleftherios P Diamandis and Theodore K. Christopoulos, Academic Press 1996, Chapters 8-19) e.g. solid-phase immunoassay e.g. Enzyme-Linked Immunosorbent Assay (ELISA), e.g. a Two-site (sandwich type, wherein an antigen is sandwiched between an immobilized antibody and a labeled antibody)

immunoassay, Avidin-Biotin immunoassay System, western blot, immunoprecipitation, Radioimmunoassay (RIA), Enzyme immunoassay, Fluorescence immunoassays (wherein florescent markers are conjugated with the antibody e.g. fluorescein, rhodamin or the like), immunoprecipitation, Chemiluminescence immunoassays (wherein organic molecules which omit light upon chemical structure modification are used e.g. isoluminol, pyrogallol, luciferin, luminol or the like), Bioluminescence immunoassays, immunoblotting techniques and the like. "Antigenic determinants" refers to the region in the antigen that is recognized by the antibody.

For binding (coating) antibodies to polystyrene microtiter wells, the antigen specific antibodies can be diluted in carbonate buffer at pH 9-9.6 as specified in the Examples below. Covalent binding has been reported (Immunoassay, Eds. Eleftherios P Diamandis and Theodore K. Christopoulos, Academic Press 1996, Chapter 24). The coating step is usually carried out by incubation of the antigen specific antibodies in the wells under the presence of a blocking solution e.g. BSA. A second antibody can be used to detect the antigen that is bound to the coating antibody. The second antibody can be labeled. Next, appropriated antigen (e.g. thrombin) standards can be prepared for the calibration curve (Immunoassay, Eds. Eleftherios P Diamandis and Theodore K. Christopoulos, Academic Press 1996, Chapter 24). The terms "coating antibody", "capture antibody" and "immobilized antibody" usually refer to an antibody that is present on the surface of a solid support. The coating antibody can be oriented so that its antigen-binding portion is available for contacting the antigen present in the sample. In the case that the detection is indirect (e.g. is carried out through a second antibody), the second detecting antibody can be generated in a different specie than the specie used to generate the capturing antibody.

The term "determining the amount of thrombin" refers to a qualitative or a quantitative determination.

The ELISA can be qualitative or quantitative. Qualitative results provide a simple positive or negative result for the presence of thrombin within the tested sample. Two or three times the standard deviation (error inherent in a test) is typically used to distinguish positive from negative samples. In quantitative ELISA, the optical density (OD) of the sample is compared to a standard curve, which is typically a serial dilution of known amounts of purified thrombin. In one embodiment of the invention, the different known concentrations of thrombin are prepared as follows: a thrombin standard solution in the concentration of 43.9 µg/ml is diluted to a concentration of 6.27 µg/ml (6270 ng/ml) in blocking buffer (1% I-Block in 0.05% Tween-20 in PBS). Next, the diluted thrombin standard solution is two-fold serially diluted (7 times) by transferring 100 µl from the previous dilution into a tube containing 100 µl of blocking buffer. Eight dilutions are prepared from 6270 down to 49 ng/ml. Next, each of the above thrombin dilutions is further diluted (1:10) in blocking buffer obtaining final thrombin concentrations of 4.9, 9.8, 19.5, 39, 78, 156.7, 313.5, and 627 ng/ml. In the next step, 100 µl of each of the final thrombin solution is transferred into a pre-coated micro-ELISA plate and the immunoassay is carried out as elaborated below without the addition of the small molecule. The immunoassays can be automated (Immunoassay, Eds. Eleftherios P Diamandis and Theodore K. Christopoulos, Academic Press 1996, Chapter 21).

In one embodiment of the invention, solid-phase immunoassay is carried out. Different solid-phase can be used, such as tubes, beads, magnetic particulate material, plastic beads, plastic support, column, small sheets and assay plates e.g. microtiter wells.

In one embodiment of the invention, the following developed two-site (sandwich Type) immunoassay is used to detect thrombin in a tested sample: in the first step, a small molecule that recognizes the substrate binding site of thrombin is added into the tested sample. The small molecule can be hirudin added to a final concentration that neutralizes at least 1 NIH unit of thrombin e.g. in an amount that neutralizes 20 NIH units of thrombin. The sample containing the thrombin can be incubated together with the small molecule for about 15 minutes. Then, the sample that comprises the small molecule is pipetted and incubated onto a solid phase, which was pre-coated with excess of thrombin specific polyclonal antibodies ("Capture antibody"). During this incubation, thrombin in the sample bounds to the capture antibody and all other sample constituents are then washed out. Next, an excess of a labeled polyclonal thrombin specific antibody is added. After incubation, the excess of labeled antibody is washed away and the signal of the bound labeled antibody is measured (e.g. by measuring the optical density [OD]). Quantification/determination of the thrombin levels can be carried out by comparison and extrapolation from a thrombin standard curve created using known amounts of purified thrombin as specified above. In this immunoassay embodiment, the same thrombin specific polyclonal antibody serves as the capture and the labeled antibody.

In an alternative embodiment, a monoclonal antibody is used as the capture antibody and as the labeled antibody. In such an embodiment, the capture and the labeled antibody are different and must recognize separate epitopes on the thrombin so they do not hinder each other's binding. In one embodiment, the thrombin specific monoclonal antibodies are not directed to the substrate binding site.

In an exemplary ELISA, a capture thrombin specific antibody e.g. a polyclonal antibody is pre-coated in excess onto a microtiter well. More specifically, the antibody solution (e.g. of protein concentration of 2 mg/ml) is diluted in the range of 1:200 to 1:100 such as 1:500 in coating buffer (50 mM Carbonate Buffer; pH=9.6) and 100 µl of the diluted antibody is added into each well. The microtiter plate is incubated over night at 2-8° C. Then, the coating solution is discarded and the microtiter plate is washed three times with 200 µl/well washing buffer (0.05% Tween-20 in PBS). Subsequently, 200 µl blocking buffer (1% I-Block in washing buffer) is added to each well and the microtiter plate is incubated at 37° C. for 1 hour. At the end of the incubation, the blocking buffer is removed. Each tested sample, such as a biological fluid, is contacted with a small molecule that recognizes the substrate binding site of thrombin. The sample can be incubated together with the small molecule for about 15 minutes. The tested samples can be diluted 1:5 in blocking buffer, and 100 µl of each diluted sample is then added into the pre-coated wells. The plate is then incubated for 1 hour at 37° C. After the incubation period, the sample solutions are discarded, the wells are washed with washing buffer. Next, a 100 µl solution comprising thrombin detecting polyclonal antibodies HRP conjugated diluted in the range of 1:200 to 1:100 such as 1:500 in blocking buffer (e.g. from a stock solution having a protein concentration of 2 mg/ml) is then added into each well. The plate is incubated for 1 hour at 37° C., washed in washing buffer as above and 100 µl 3,3',5,5'-Tetramethylbenzidine (TMB) Liquid Substrate System for ELISA (HRP substrate) is added to each well. The plate is incubated at room temperature for about 60 minutes (until a strong blue color is observed in wells containing a high thrombin concentration). The reaction is stopped by adding 100 µl stop solution (1 M Hydrochloric Acid) to each well. The plate is read at $OD_{450\ nm}$ and the precise thrombin concentration in the sample can be extrapolated by comparison to a thrombin standard curve prepared from known thrombin concentrations as described above. Typically, the linear range of the thrombin standard curve is used to calculate the precise thrombin concentration in the tested sample.

In one embodiment of the invention, the capture antibody is a polyclonal anti-human thrombin sheep antibodies (e.g. an antibody as manufactured by Affinity Biologicals; Catalog No. SAHT-AP). In another embodiment of the invention, the immunogen used for raising the polyclonal antibody is thrombin prepared from purified human prothrombin, with the active site blocked with PPACK. In another further embodiment of the invention, the detecting antibody is sheep anti-human thrombin antibody HRP conjugated (e.g. an antibody as manufactured by Affinity Biologicals; Catalog No. SAHT-HRP).

In another embodiment of the invention, an indirect ELISA assay is used. In an exemplary indirect ELISA, the tested sample is contacted with a small molecule that recognizes the substrate binding site of thrombin such as the fibrinogen binding site and then added to a solid phase e.g. a well of a microtiter plate, where it is given time to adhere to the plastic e.g. through charge interaction. Next, a solution of non-reacting protein, such as bovine serum albumin or casein, is added to block any plastic surfaces in the well that remain uncoated by the antigen present within the tested sample. In the next step, the primary antibody which binds specifically to the thrombin is added into each well. Afterwards, a secondary antibody that binds the primary antibody is added into each well. The secondary antibody has an enzyme attached to it, which has a negligible effect on the binding properties of the antibody. Then, a substrate for this enzyme is added. This substrate changes color upon reaction with the enzyme. The color change shows that secondary antibody has bound to the primary antibody. Typically, the plate is washed following the addition of the primary and secondary antibodies so that unbound antibodies are removed. In an alternative embodiment, one antibody linked to an enzyme is used to detect the presence of thrombin within the sample. A spectrometer is used to give quantitative values for the color strength. The detectable signal can be radioactive (e.g. radioactive iodine, tritium, carbon, sulfur or the like), colorimetric, fluorescent signal and the like.

The invention provides a kit for quantifying thrombin in a sample comprising anti-thrombin III (AT-III), the kit comprises the following components: a thrombin specific polyclonal antibody and a small molecule that recognizes the substrate binding site of thrombin, wherein the thrombin specific antibody is raised against a thrombin having a blocked active site. The kit can comprise instructions for use and/or purified thrombin for preparing a standard curve. The components of the kit can be provided as powders, solutions, and/or combination thereof. The solutions can be provided in frozen form. The disclosure of applications, patents and publications, cited above or below, is hereby incorporated by reference.

The following examples are illustrative but not limiting.

EXAMPLES

Material and Methods

Immunoassay Procedure:
1. Coating a Micro-ELISA Plate with a Capture Antibody.
A micro-ELISA plate (96 wells; Costar; Catalog No. 9018) was coated with polyclonal anti-human thrombin sheep antibodies (Affinity Biologicals; Catalog No. SAHT-AP; The immunogen used for raising the polyclonal antibody was thrombin prepared from purified human prothrombin, with the active site blocked with PPACK). The coating procedure was carried out as follows: the antibodies were diluted 1:500 in coating buffer (50 mM Carbonate Buffer; pH=9.6; Sigma; Catalog No. C-3041) and 100 µl of the diluted antibodies was added into each well. The micro-ELISA plate was then incubated over night (for about 16 hours) at 2-8° C. Then, the coating solution was discarded and the wells were washed three times with 200 µl/well washing buffer [0.05% Tween-20 (Sigma; Catalog No. P-1379) in PBS (Biological Industries; Catalog No. 02-023-SA)]. Subsequently, 200 µl blocking buffer [1% I-Block (Tropix; Catalog No. AI300) in washing buffer] was added into each well and the ELISA plate was incubated at 37° C. for 1 hour. The blocking buffer was removed before addition of the tested sample.

2. Addition of the Tested Samples and the Labeled Bound Antibody into the Pre-Coated Wells and Measuring the Signal of the Labeled Bound Antibody.

The tested samples were diluted 1:5 in blocking buffer, and 100 µl of each diluted sample was added into the pre-coated micro-ELISA plate. The plate was then incubated for 1 hour at 37° C. After the incubation period, the sample solutions were discarded, the wells were washed three times with 200 µl/well washing buffer as specified above, and 100 µl anti-thrombin antibodies HRP conjugated (Affinity Biologicals; Catalog No. SAHT-HRP; diluted 1:500 in blocking buffer; "labeled antibody") was added into each well. Untreated pig plasma served as negative control. Known concentrations of thrombin (4.9 to 627 ng/ml) in blocking buffer were used as positive control. The OD results of the negative and positive control groups are not presented in the results shown below. The plate was incubated for 1 hour at 37° C., washed three times with 200 µl/well washing buffer as specified above, and 100 µl 3,3',5,5'-tetramethylbenzidine (TMB- an HRP substrate; Sigma, Catalog No. T-0440) was added into each well. The plate was incubated at room temperature (about 22±3° C.) for about 60 minutes (until a strong blue color was observed in wells containing the highest thrombin concentration). The reaction was stopped by adding 100 µl stop solution (1 M Hydrochloric Acid; Riedel de Haen; Catalog No. 30721) into each well. The plate was read at $OD_{450\,nm}$. An increase in the obtained OD value indicates on a higher thrombin concentration in the sample. The precise thrombin concentration in the sample is extrapolated by comparison to a thrombin standard curve created using known amounts of purified thrombin. The linear range of the thrombin standard curve is used to calculate the precise thrombin concentration in the sample.

Preparation of Different Concentrations of Thrombin Used in the Examples Below:

For the preparation of different thrombin concentrations, an Omrix in house standard (43.9 µg/ml) was used. To obtain the different concentrations, the thrombin standard was diluted to a concentration of 6.27 µg/ml (6270 ng/ml) in blocking buffer (see components above). Next, the diluted thrombin standard solution was two-fold serially diluted (7 times) by transferring 100 µl from the previous dilution into a tube containing 100 µl of blocking buffer. Eight dilutions were prepared from 6270 down to 49 ng/ml. Next, each of the above thrombin dilutions was further diluted (1:10) into the tested sample.

Example 1

Sandwich ELISA for Detecting Thrombin in a Sample

A two-site (sandwich Type) immunoassay was developed to detect thrombin in a tested sample. Briefly, the sample containing the thrombin was pipetted onto a solid phase, which was pre-coated with excess of polyclonal anti-thrombin antibodies ("Capture antibody"), and incubated as elaborated in the Material and Methods section. During this incubation, thrombin in the sample bounds to the capture antibody and all other sample constituents are then washed out. Next, an excess of labeled anti-thrombin antibody was added. After incubation, the excess of labeled antibody was washed away. In this immunoassay, the same polyclonal antibody served as the capture and the detection/labeled antibody. The polyclonal antibody was an affinity purified IgG sheep anti human thrombin. The antibodies were raised by using as immunogen purified human thrombin (prepared from purified prothrombin) with the active site/catalytic site blocked with PPACK. PPACK is a peptide which binds to the catalytic site of thrombin.

In this experiment, the ability of the above developed immunoassay to detect thrombin levels in a sample was examined. For this purpose, samples containing increasing thrombin concentrations in blocking buffer were prepared (final thrombin concentrations in the sample of about: 4.9, 9.8, 19.5, 39, 78, 156.7, 313.5, and 627 ng/ml prepared as elaborated above) and the immunoassay was carried out as specifically elaborated in the above Material and Methods section. The signal of the labeled bound antibody was detected in each sample and the results are presented in FIG. 1.

Figure 1:
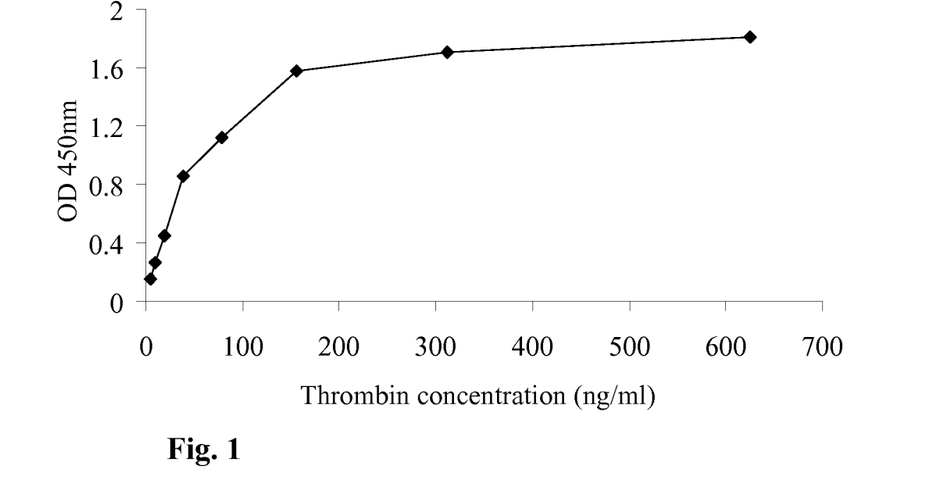
FIG. 1 shows the performance (OD values) of an immunoassay developed for the determination of thrombin levels in a buffer sample.

It was found that the signal of the bound antibody is directly related to the concentration of thrombin in a sample containing precise concentrations of thrombin in buffer. The five lowest dilutions were within the linear range.

It was therefore concluded that this immunoassay is a tool that can be used to determine the level of thrombin in a tested buffer sample comprising thrombin (by comparison to a thrombin standard curve created using known amounts of purified thrombin).

Example 2

Figure 2:
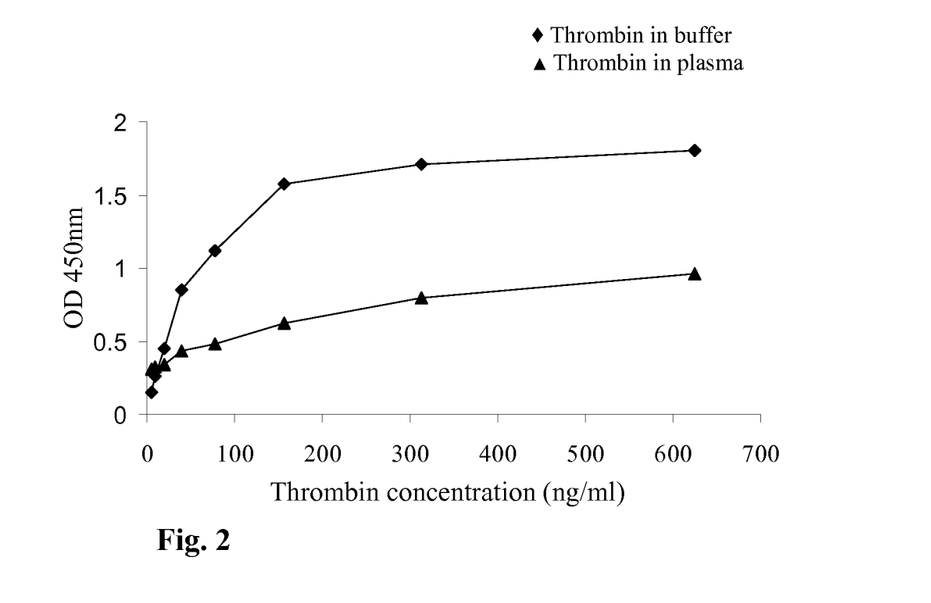
FIG. 2 shows the OD values obtained by the thrombin specific immunoassay in samples comprising increasing concentrations of thrombin in buffer (♦) as compared to the OD values obtained in plasma samples spiked with increasing concentrations of thrombin (▲).

Interference of Substances Present in the Plasma with the Detection of Thrombin by the Thrombin Specific Immunoassay The previous experiment shows the ability of the above immunoassay to detect thrombin in a buffer sample containing thrombin. In this experiment, the ability of the above-developed immunoassay to detect thrombin in pig plasma samples (obtained from the Institute of animal research, Kibutz Lahav Israel) that were spiked with increasing concentrations of thrombin (the same as in Example 1) was examined Comparable thrombin concentrations in blocking buffer were used as reference. The immunoassay was carried out as above, and the obtained OD values for both groups [i.e. group 1-plasma samples spiked with thrombin (▲); and group 2-buffer sample comprising thrombin (♦)] are shown in FIG. 2.

It can be seen that the OD results obtained for thrombin in plasma were much lower than the OD results obtained for thrombin in blocking buffer in the same thrombin concentration. It was therefore found that the immunoassay is compromised by interfering substances present in the plasma.

Example 3

Interference of AT-III with the Detection of Thrombin by the Thrombin Specific Immunoassay Example 2 shows that there are substances in the plasma that interfere with the thrombin specific immunoassay. The normal AT-III concentration in human blood plasma is high and is approximately 0.12 mg/ml. The following experiment was carried out in order to examine whether the AT-III present in the plasma is the factor that interferes with the immunoassay.

For this purpose, samples with AT-III (American diagnostica; Catalog No. 433; diluted in blocking buffer to a final concentration of 1 IU/ml) or without AT-III (blocking buffer solution as indicated above) were prepared. Next, different concentrations of thrombin were added into these samples (final concentrations of 4.9, 9.8, and 19.5 ng/ml prepared as elaborated above). The immunoassay was carried out as elaborated above to detect thrombin in the samples.

Figure 3:
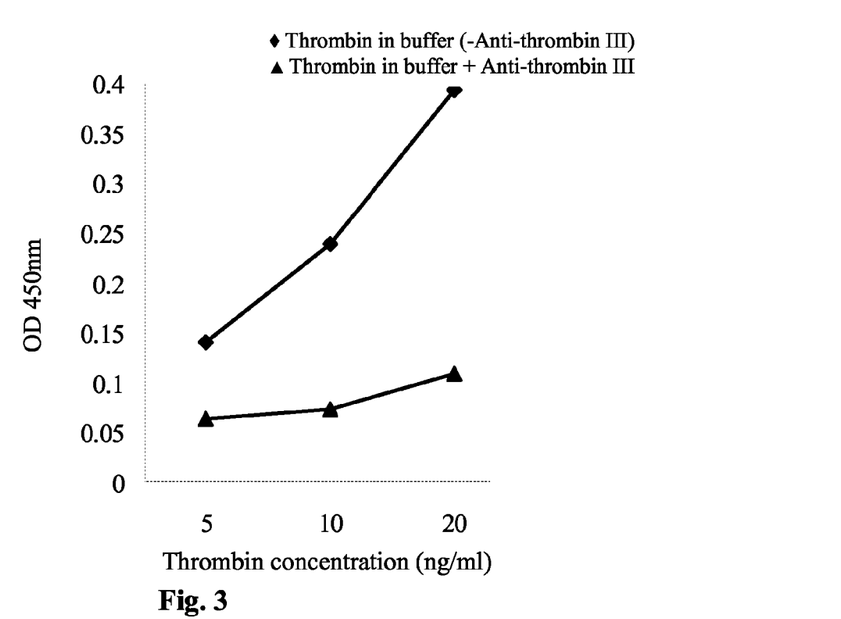
FIG. 3 shows the OD values obtained by the thrombin specific immunoassay in samples comprising increasing concentrations of thrombin in buffer and containing AT-III (▲) and in samples comprising increasing concentrations of thrombin in buffer in the absence of AT-III (♦).

It can be seen that the OD results obtained in the presence of AT-III were much lower than the OD results obtained in the absence of AT-III (FIG. 3).

It was found that AT-III causes interference in the thrombin immunoassay and therefore, it indicates that the interference detected in the plasma (Example 2) may be, at least in part, accounted to the presence of AT-III.

Example 4

The Beneficial Effect of Hirudin Addition in an Immunoassay for Detecting Thrombin in Plasma Hirudin is a small peptide of 65 amino acids that occurs naturally in leeches and has blood anticoagulant properties. Hirudin binds to the fibrinogen binding site (the substrate binding site) in the thrombin whereas AT-III binds to the catalytic site/active site in the thrombin. In the following set of experiments, the effect of hirudin addition on AT-III interference in the thrombin specific immunoassay was examined.

For this purpose, different solutions containing AT-III were prepared [see solutions 1, 4 and 7 below] and different concentrations of hirudin were mixed into the different solutions (see groups 2, 3, 5, 6, 8 and 9 below). Next, different concentrations of thrombin were added into the mixtures and the immunoassay was carried out.

Preparation of solutions 1-9:
1. AT-III (American diagnostica; Catalog No. 433) diluted in blocking buffer to a final concentration of 1 IU/ml.
2. A solution as in 1+hirudin (Sigma; Catalog No. 94581) in a final concentration of 1 U/ml (1 U of hirudin corresponds to 1 ATU (antithrombin unit [ATU]; 1 ATU is defined as the amount of inhibitor that neutralizes 1 NIH unit of thrombin).
3. A solution as in 1+only hirudin was added to a final concentration of 5 U/ml.
4. A solution as in 1+heparin (Pharmacare) in a final concentration of 10 IU/ml. Heparin increases the inactivation of thrombin by AT-III.
5. A solution as in 4+hirudin in a final concentration of 1 U/ml.
6. A solution as in 4+hirudin in a final concentration of 5 U/ml.
7. Pig plasma.
8. As in 7+hirudin in a final concentration of 1 U/ml.
9. As in 7+hirudin in a final concentration of 5 U/ml.

Next, thrombin was added into each solution (1-9) in a final concentration of 4.9, 9.8, 19.5, 39, 78, 156.7, 313.5, and 627 ng/ml in the manner elaborated above (see the Materials and Methods section). In this experiment, thrombin was added into solutions 2, 3, 5, 6, 8 and 9 which contain hirudin together with AT-III.

The prepared samples (solutions 1-9 mixed with the different thrombin concentrations) were diluted, pipetted into a pre-coated ELISA plate, and the OD levels were determined as specified in the Materials and Methods section.

Figure 4:
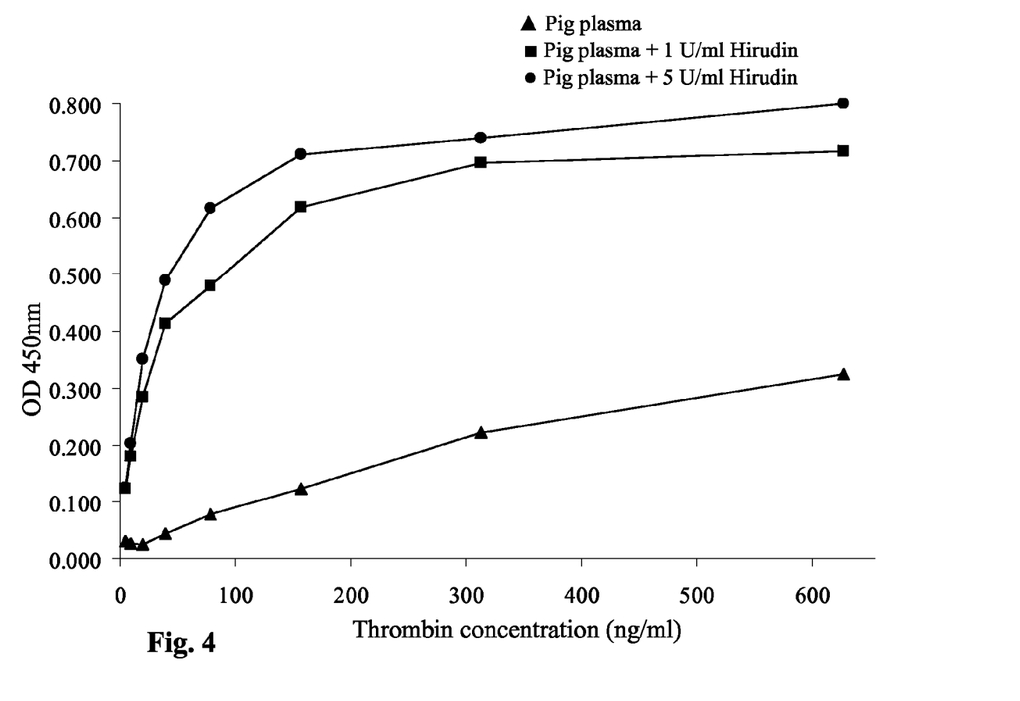
FIGS. 4-6 show the effect of addition of a mixture of hirudin and plasma (FIG. 4), hirudin and AT-III (FIG. 5) or hirudin, AT-III and heparin (FIG. 6) to thrombin samples on detection of thrombin by the immunoassay.
Figure 5:
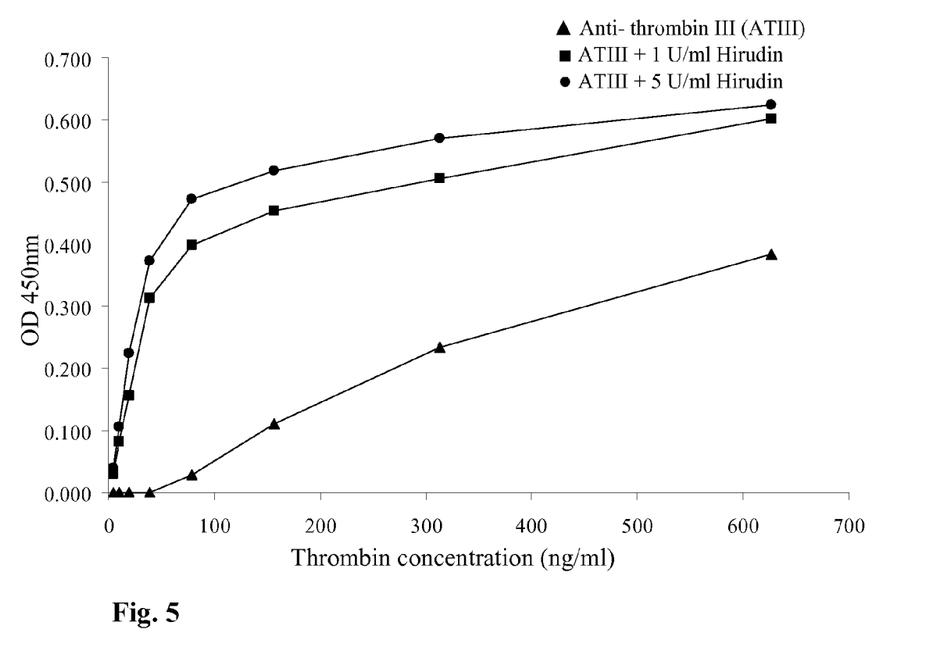
Figure 6:
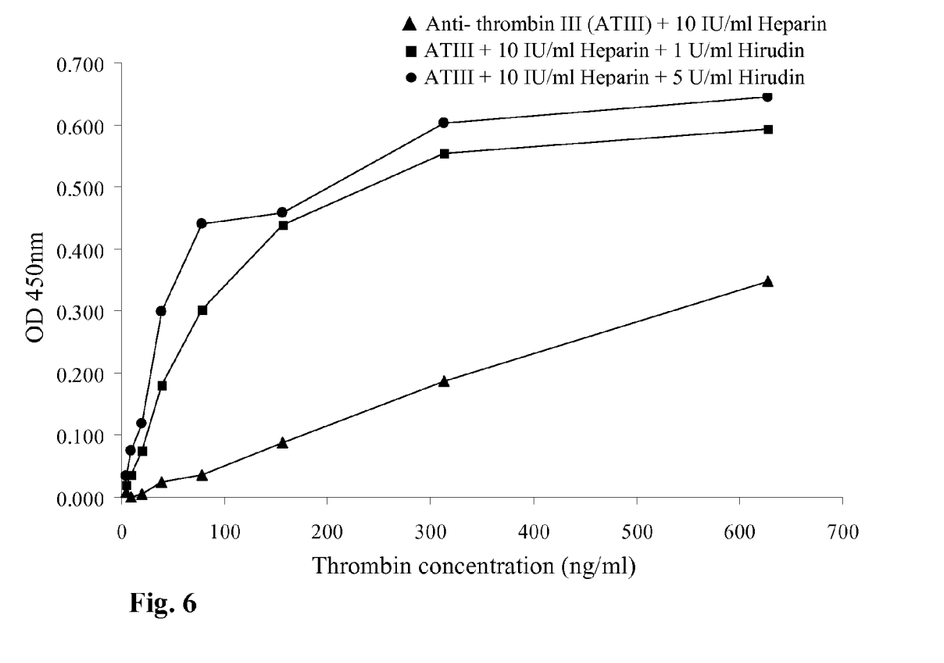

The OD values of the different samples containing thrombin are shown in FIGS. 4, 5 and 6. In FIG. 4 the sample is pig plasma (samples prepared with solutions 7-9). In FIG. 5 the sample is a solution comprising AT-III (samples prepared with solutions 1-3). In FIG. 6 the sample is a solution comprising AT-III and heparin (samples prepared with solutions 4-6).

It was observed that addition of hirudin decreases, in a dose-dependent manner, the AT-III interference on the thrombin specific immunoassay.

These results indicate that in order to improve thrombin detection by the thrombin specific immunoassay in a sample comprising AT-III, it is beneficial to add to the tested sample hirudin, a small molecule capable of binding to the substrate binding site of thrombin.

Example 5

The Beneficial Effect of Hirudin Addition in a Thrombin Specific Immunoassay for Detecting Thrombin in Plasma The results of the above experiment indicate that addition of hirudin to a sample comprising AT-III improves thrombin detection in a specific immunoassay. In the above experiment, thrombin was added into samples which contain hirudin together with AT-III. However, a tested plasma sample already contains thrombin, and most of the thrombin is attached to anti-thrombin III. In such a case, hirudin will need to act on a thrombin-AT-III complex. The following experiment examines the beneficial effect of hirudin in an immunoassay for detecting thrombin in a plasma sample which already contains thrombin and AT-III.

Figure 7:
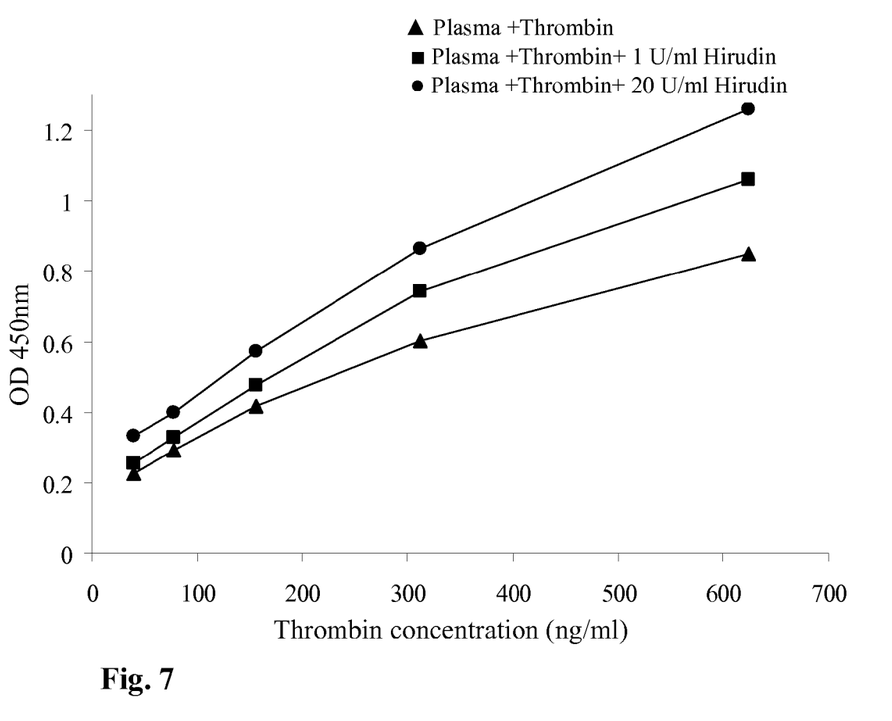
FIG. 7 shows the increase of thrombin detection levels in plasma samples using the thrombin specific immunoassay by addition of hirudin to the samples.

In the following set of experiment, various concentrations of thrombin were spiked into samples of pig plasma (at final concentrations of 4.9 to 627 ng/ml; see preparation of samples in the Materials and Methods section). Three groups of samples were prepared. In the next step, hirudin was added into two of the groups at a final concentration of 1 U/ml (■) or 20 U/ml (●). To the third group no hirudin was added, this group was used as a control (▲). Thrombin was detected in the different groups by the ELISA assay described above. In this experiment, non spiked pig plasma supplemented with 5 U/ml hirudin was used as a negative control (results of the negative control are not shown). The results are shown in FIG. 7.

The mole ratio between hirudin added to the sample and thrombin present in the sample is shown in Table 1 below.

TABLE 1

The mole ratio between hirudin and thrombin in the tested sample

| Thrombin Concentration in the sample (ng/ml) | Thrombin units in the sample* (U/ml) | Hirudin:thrombin Mole Ratio when 1 ATU/ml Hirudin was added | Hirudin:thrombin Mole Ratio when 20 ATU/ml Hirudin was added |
|---|---|---|---|
| 4.9 | 0.01225 | 81.63 | 1632.65 |
| 9.8 | 0.0245 | 40.82 | 816.33 |
| 19.6 | 0.049 | 20.41 | 410.26 |
| 39.2 | 0.098 | 10.20 | 205.13 |
| 78.4 | 0.196 | 5.10 | 102.56 |
| 156.8 | 0.392 | 2.55 | 51.05 |
| 313.6 | 0.784 | 1.27 | 25.52 |
| 627.2 | 1.568 | 0.64 | 12.76 |

*1 thrombin U is equivalent to about 400 ng/ml thrombin.

It was found that addition of hirudin to a sample of plasma spiked with thrombin resulted in a hirudin concentration-depended increase in the ability to detect thrombin in the immunoassay. The results also show that when the mole ratio between hirudin and thrombin was higher than or equal to 0.637755, an increase in the ability of the immunoassay to detect thrombin was observed.

The invention claimed is:

1. An in vitro immunoassay for quantifying thrombin in a sample in the presence of anti-thrombin III (AT-III), the immunoassay comprising the steps of: contacting the sample with a small molecule that recognizes a substrate binding site of thrombin and is selected from the group consisting of naturally occurring hirudin, synthetic hirudin variants, hirudin derivatives, recombinant hirudin variants, hirudin mimics, and a combination thereof; adding to the sample mixture a thrombin specific antibody, wherein the thrombin specific antibody consists of a polyclonal antibody or a fragment thereof and was raised against a thrombin having a blocked active site with a molecule selected from the group consisting of Phe-Pro-Arg-chloromethylketone (PPACK), 4-aminophenylpyruvic acid (APPA), 4-(2-aminoethyl)benzenesulfonyl fluoride (AEBSF), and a combination thereof; measuring the binding of the polyclonal antibody or fragment thereof to thrombin in the sample mixture; and quantifying the amount of thrombin by comparison and extrapolation from a predetermined thrombin standard curve using known amounts of purified thrombin.

2. The immunoassay according to claim 1, wherein the sample is a biological specimen selected from the group consisting of blood or blood components selected from the group consisting of plasma and blood derived fractions comprising thrombin and AT III.

3. The immunoassay according to claim 1, wherein the immunoassay is a solid-phase immunoassay.

4. The immunoassay according to claim 1, wherein the immunoassay is a solid-phase sandwich immunoassay.

5. An in vitro immunoassay for quantifying thrombin in a sample comprising anti-thrombin III (AT-III) and thrombin, the immunoassay comprises the steps of: contacting the sample with a small molecule that recognizes a substrate binding site of thrombin and is selected from the group consisting of naturally occurring hirudin, synthetic hirudin variants, hirudin derivatives, recombinant hirudin variants, hirudin mimics, and a combination thereof; contacting the sample mixture with a thrombin specific antibody that consists of a polyclonal antibody or a fragment thereof and was raised against a thrombin blocked in the active site with a molecule selected from the group consisting of Phe-Pro-Arg-chloromethylketone (PPACK), 4-aminophenylpyruvic acid (APPA), 4-(2-aminoethyl)benzenesulfonyl fluoride (AEBSF), and a combination thereof; and measuring the level of thrombin by detecting bound polyclonal antibody or fragment thereof and extrapolating the amount of thrombin from a predetermined thrombin standard curve using known amounts of purified thrombin.

6. The immunoassay according to claim 5, wherein the sample is a biological specimen selected from the group consisting of blood or blood components selected from the group consisting of plasma and blood derived fractions comprising thrombin and AT III.

7. The immunoassay according to claim 5, wherein the immunoassay is a solid-phase immunoassay.

8. The immunoassay according to claim 5, wherein the immunoassay is a solid-phase sandwich immunoassay.

* * * * *